US008805486B2

(12) United States Patent
Giorgis et al.

(10) Patent No.: US 8,805,486 B2
(45) Date of Patent: Aug. 12, 2014

(54) DEVICE FOR THE ANALYSIS OF AN ENDOCARDIAC SIGNAL OF ACCELERATION

(71) Applicant: Sorin CRM S.A.S, Clamart Cedex (FR)

(72) Inventors: Lionel Giorgis, Rennes (FR); Alfredo Hernandez, Rennes (FR)

(73) Assignee: Sorin CRM S.A.S., Clamart Cedex (FR)

( * ) Notice: Subject to any disclaimer, the term of this patent is extended or adjusted under 35 U.S.C. 154(b) by 0 days.

(21) Appl. No.: 14/046,622

(22) Filed: Oct. 4, 2013

(65) Prior Publication Data
US 2014/0039335 A1 Feb. 6, 2014

Related U.S. Application Data

(63) Continuation of application No. 12/389,291, filed on Feb. 19, 2009, now Pat. No. 8,554,313.

(30) Foreign Application Priority Data

Feb. 20, 2008 (FR) ...................................... 08 00907

(51) Int. Cl.
*A61B 5/04* (2006.01)
*A61N 1/00* (2006.01)

(52) U.S. Cl.
USPC ........................................... 600/513; 607/27

(58) Field of Classification Search
USPC ......... 600/508–509, 512–514; 607/17–26, 27
See application file for complete search history.

(56) References Cited

U.S. PATENT DOCUMENTS

| 5,304,208 A | 4/1994 | Inguaggiato et al. |
| 5,496,351 A | 3/1996 | Plicchi et al. |
| 6,556,866 B2 | 4/2003 | Dal Molin et al. |

(Continued)

FOREIGN PATENT DOCUMENTS

| EP | 0 515 319 A2 | 11/1992 |
| EP | 0 655 260 | 5/1995 |

(Continued)

OTHER PUBLICATIONS

Bombardini et al., Peak Endocardial Acceleration Reflects Heart Contractility Also in Atrial Fibrillation, PACE—Pacing and Clinical Electrophysiology, vol. 23, No. 9, dated Sep. 1, 2000, 5 pages.

(Continued)

*Primary Examiner* — Catherine Voorhees
(74) *Attorney, Agent, or Firm* — Foley & Lardner LLP

(57) ABSTRACT

Devices and methods related to endocardial acceleration signal processing are provided. One device is configured to: (1) divide an endocardial acceleration (EA) signal into a plurality of EA sub-signals; (2) identify, in each of the plurality of EA sub-signals, at least one signal component associated with a type of heart sound; (3) extract a characteristic of the at least one signal component for two or more of the plurality of cycles; (4) calculate a correlation coefficient correlating the at least signal component for a first cycle of the plurality of cycles to the at least one signal component of a second cycle of the plurality of cycles; and (5) perform temporal retiming of one or more of the signal components based on the correlation coefficient to generate one or more adjusted signal components of the associated one or more EA sub-signals.

23 Claims, 6 Drawing Sheets

(56) References Cited

U.S. PATENT DOCUMENTS

| | | |
|---|---|---|
| 7,139,609 B1 | 11/2006 | Min et al. |
| 7,613,507 B2 | 11/2009 | Vitali et al. |
| 7,664,547 B2 | 2/2010 | Plicchi et al. |
| 2003/0060723 A1 | 3/2003 | Joo et al. |
| 2003/0135126 A1 | 7/2003 | Kuo |
| 2003/0204146 A1 | 10/2003 | Carlson |
| 2004/0059237 A1 | 3/2004 | Narayan et al. |
| 2005/0131470 A1 | 6/2005 | Vitali et al. |
| 2005/0209649 A1* | 9/2005 | Ferek-petric ............ 607/17 |
| 2006/0020294 A1 | 1/2006 | Brockway et al. |
| 2006/0094967 A1 | 5/2006 | Bennett et al. |
| 2006/0111642 A1 | 5/2006 | Baura et al. |
| 2006/0189874 A1* | 8/2006 | Vitali et al. ............ 600/513 |
| 2006/0293715 A1 | 12/2006 | Plicchi et al. |
| 2007/0032733 A1 | 2/2007 | Burton |
| 2007/0112275 A1 | 5/2007 | Cooke et al. |
| 2007/0239218 A1 | 10/2007 | Carlson et al. |

FOREIGN PATENT DOCUMENTS

| | | |
|---|---|---|
| EP | 1 108 466 | 6/2001 |
| EP | 1 736 203 | 12/2006 |
| EP | 1 741 387 | 1/2007 |

OTHER PUBLICATIONS

Plicchi et al., PEA I and PEA II Based Implantable Haemodynamic Monitor: Pre Clinical Studies in Sheep, Europace: Journal of the European Society of Cardiology, vol. 4, No. 1, 2002, 6 pages.

Preliminary Search Report for French Patent Application No. 0800907, dated Oct. 6, 2008, 3 pages.

* cited by examiner

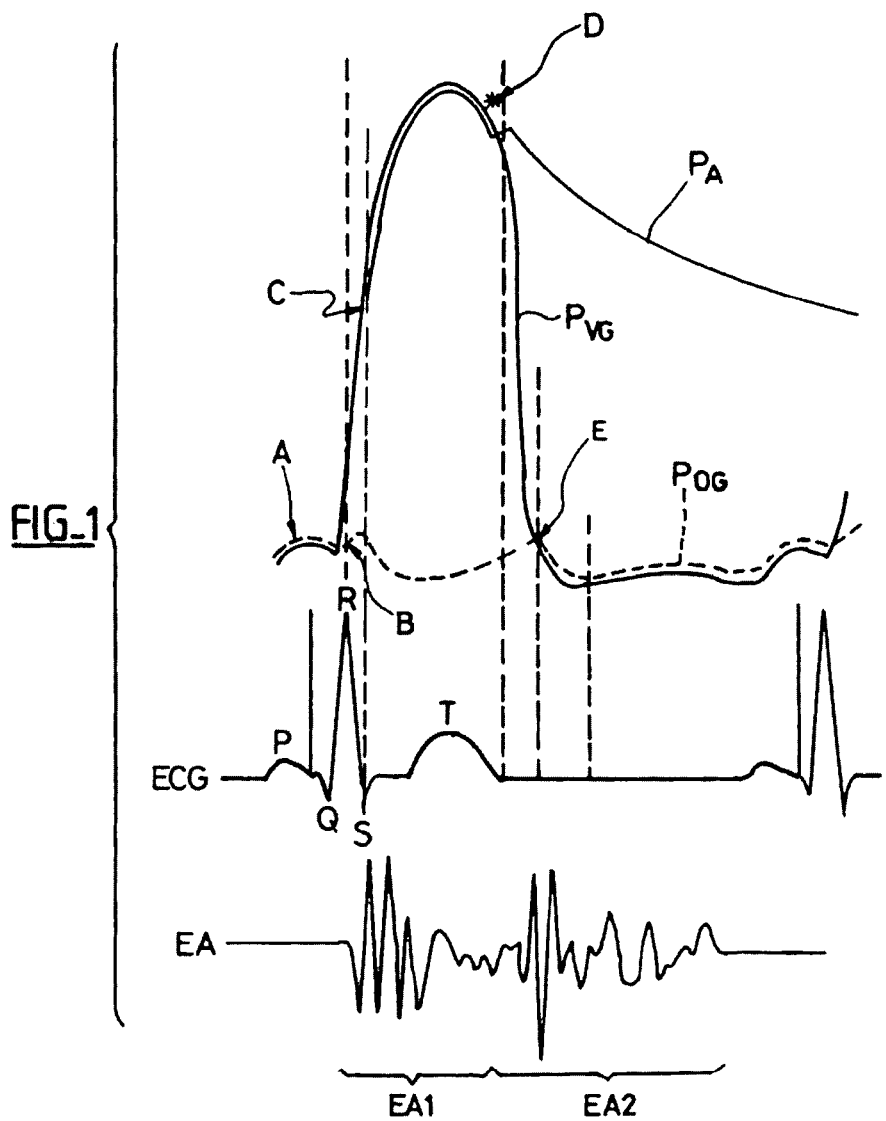
FIG_1
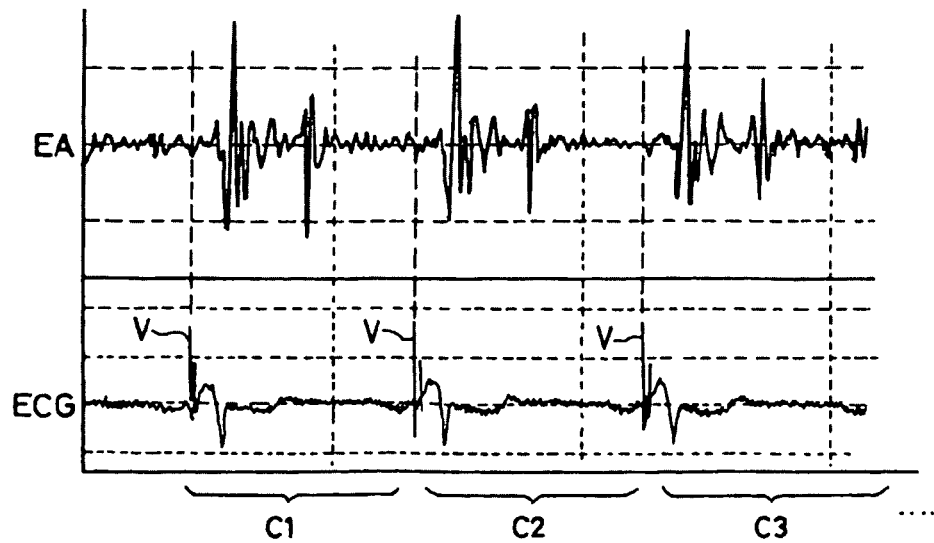
FIG_3

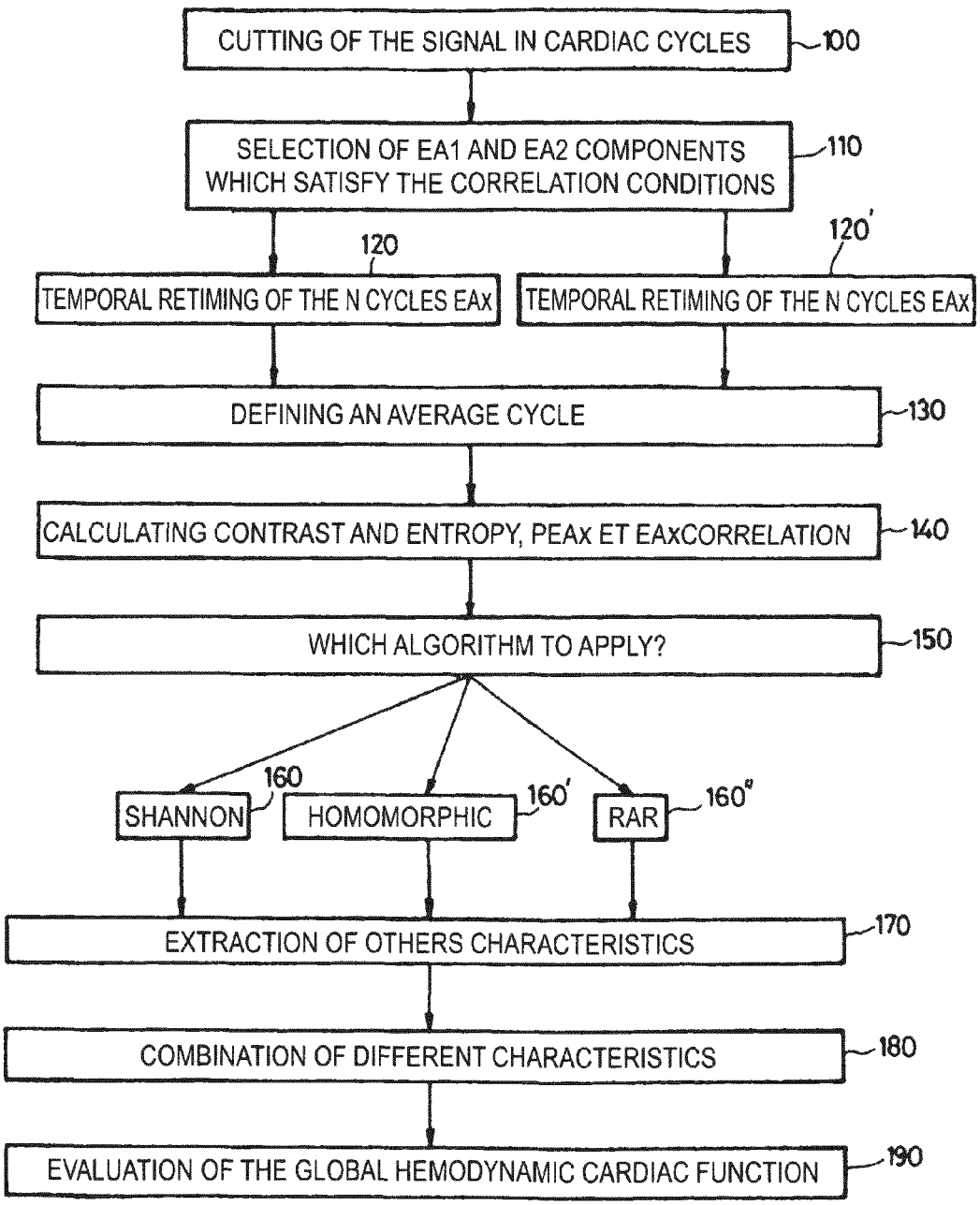

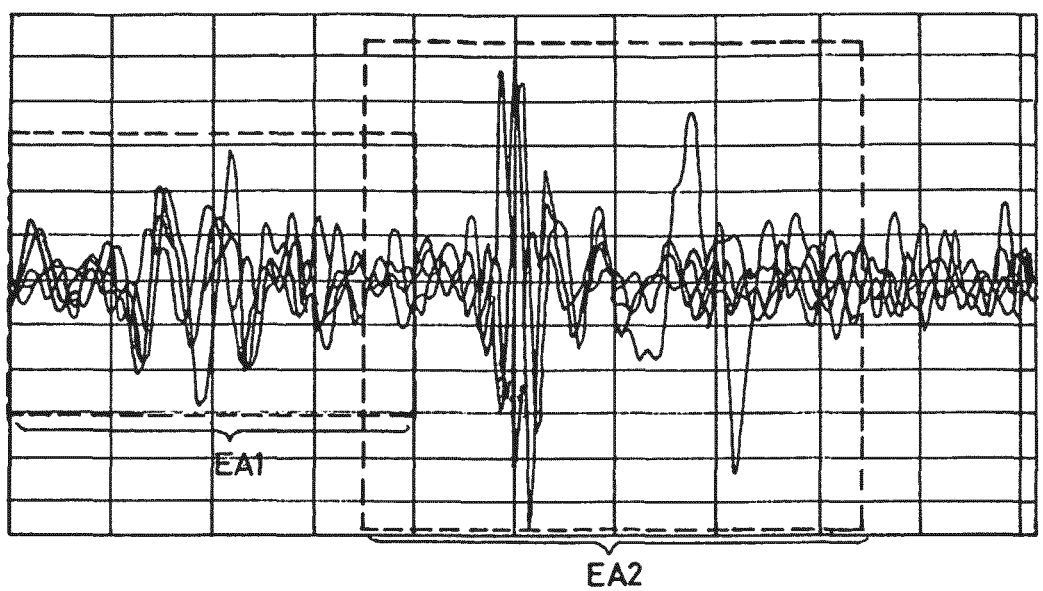
FIG_4
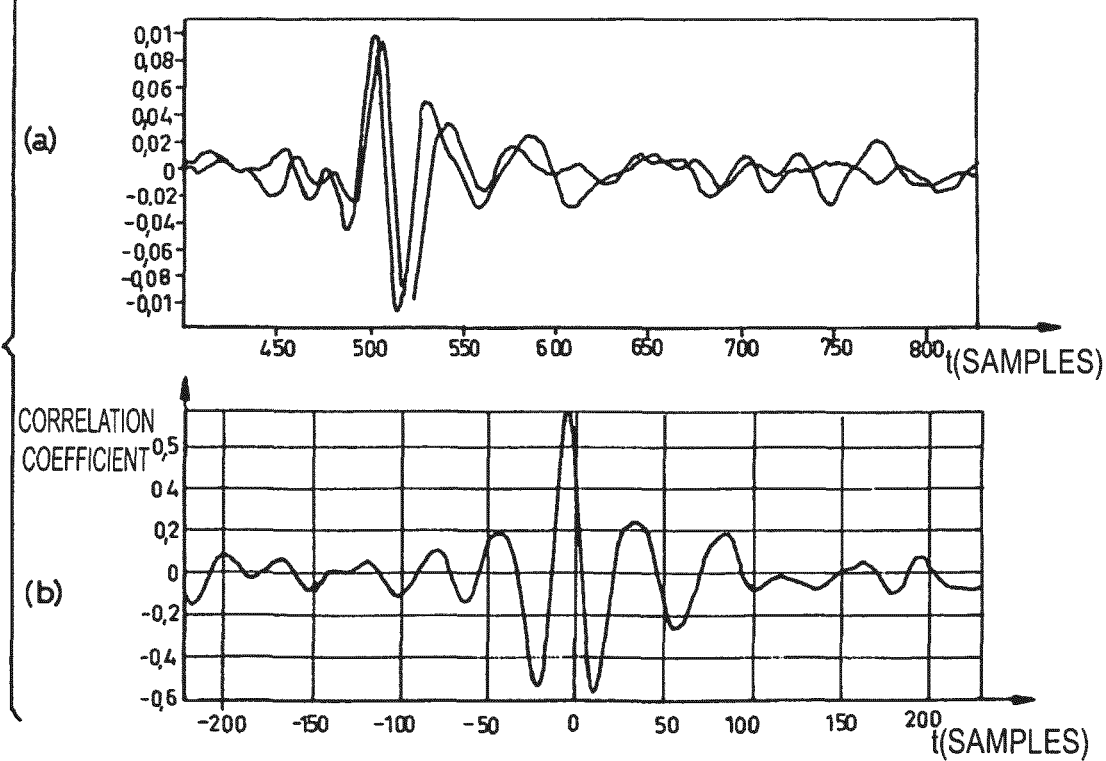
FIG_5

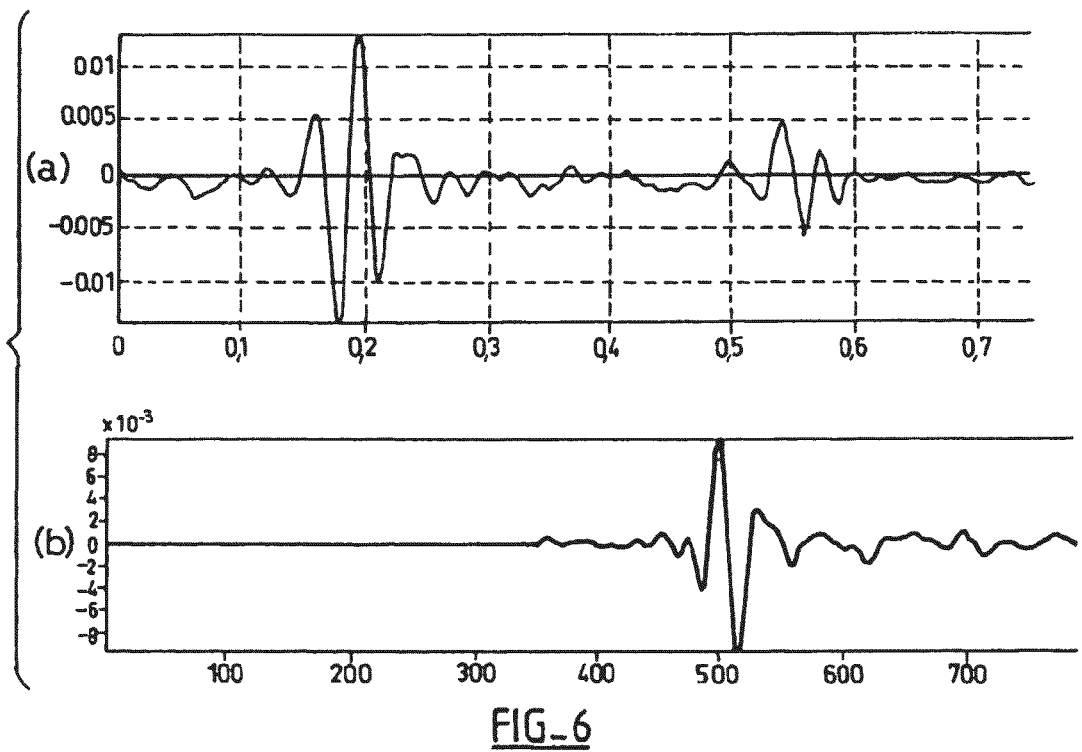
FIG_6
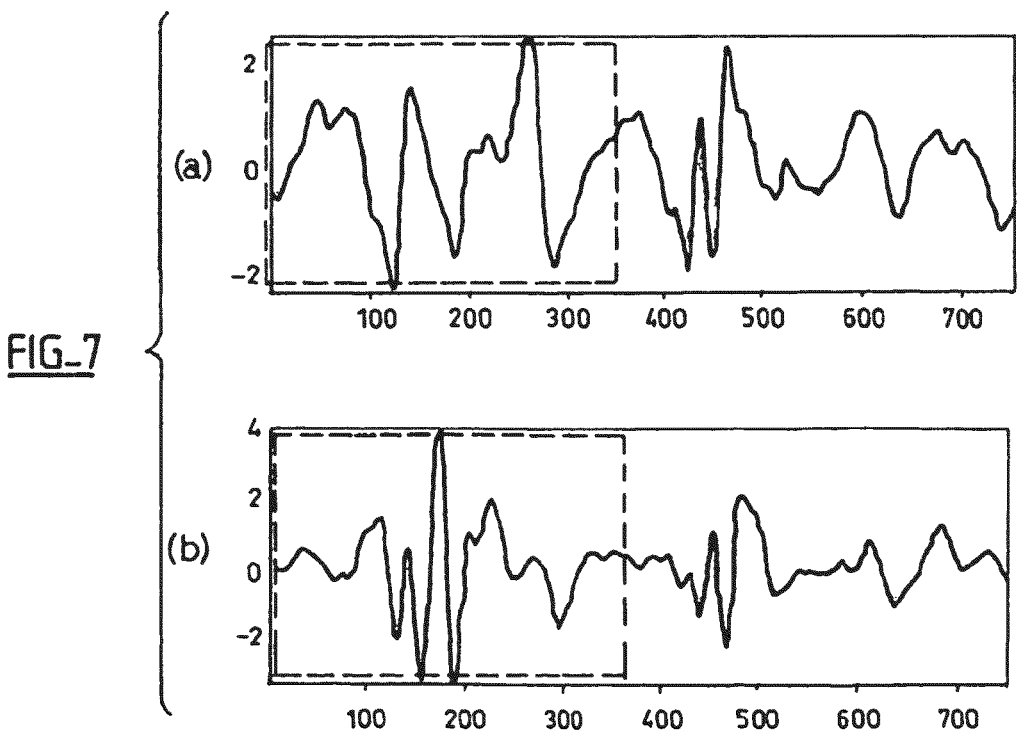
FIG_7

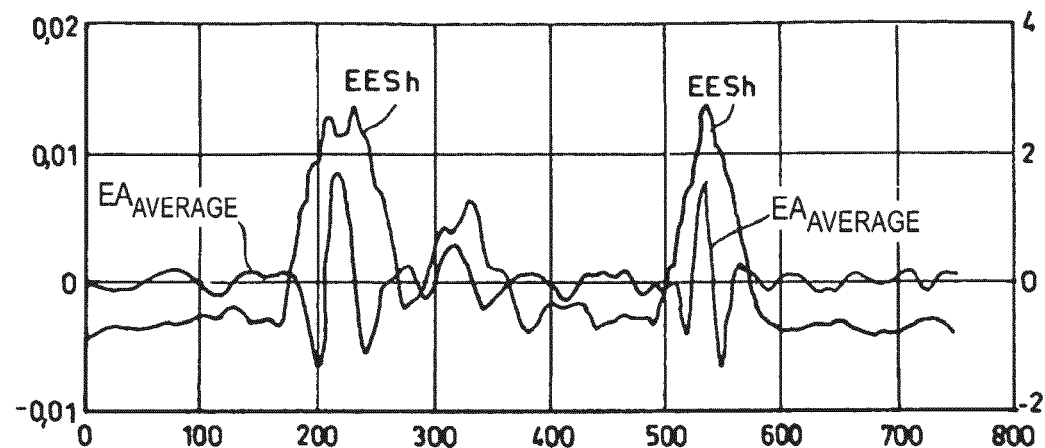
FIG_8
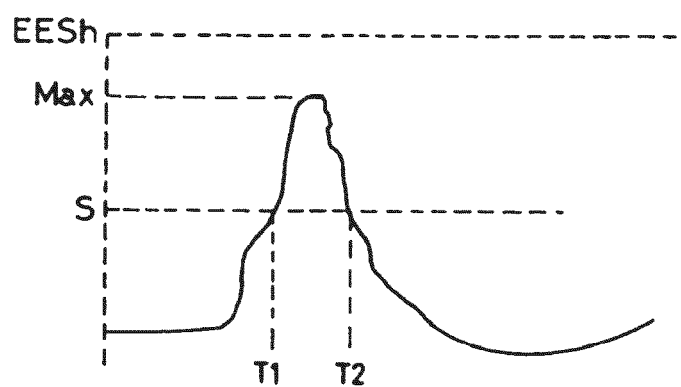
FIG_9a
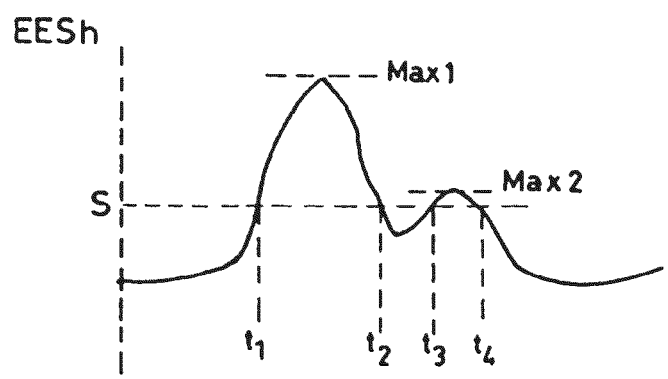
FIG_9b

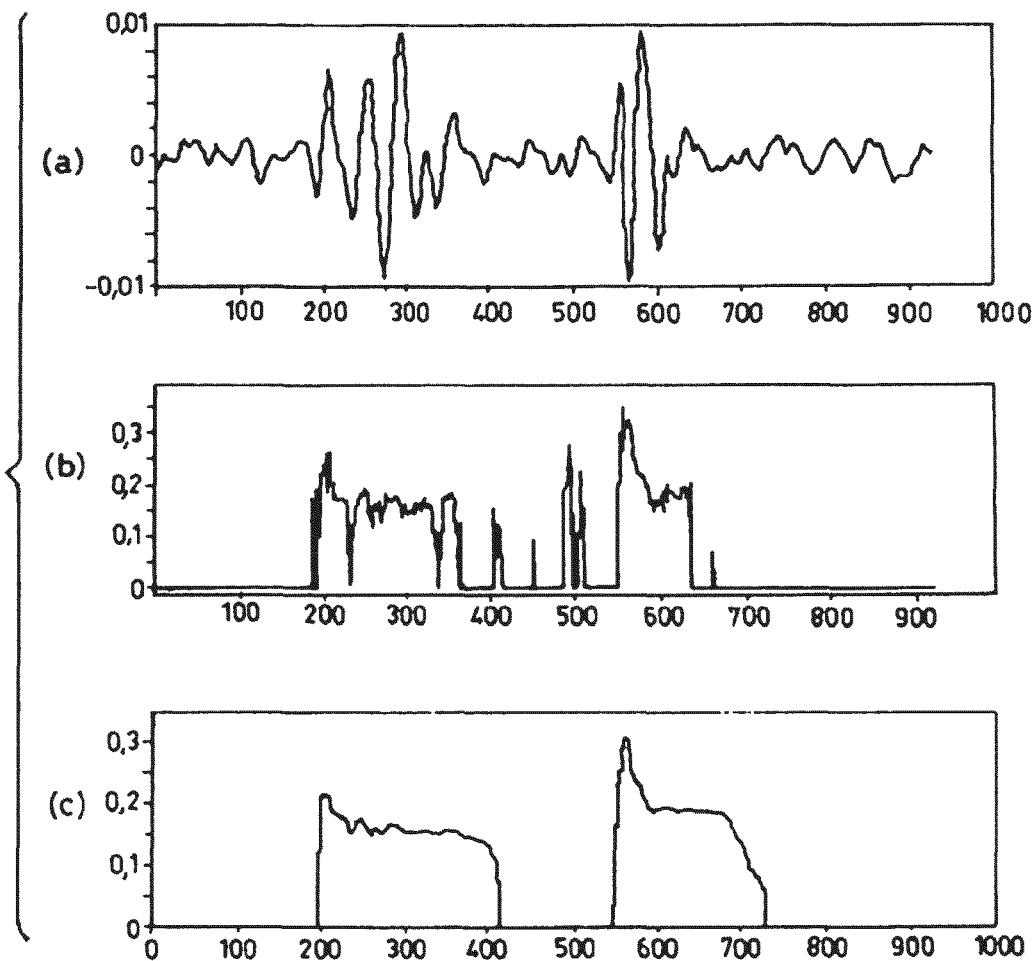
FIG_10
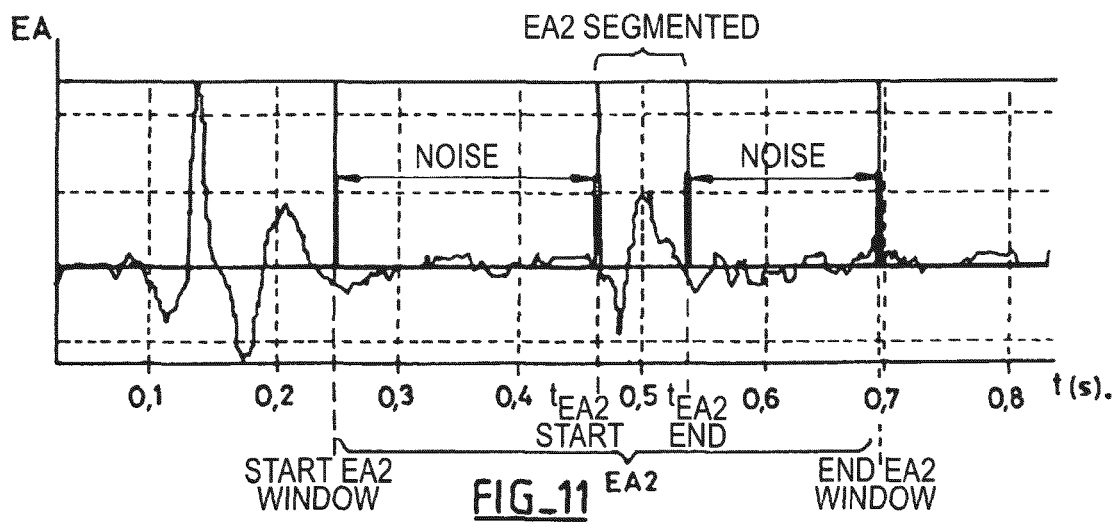
FIG_11

DEVICE FOR THE ANALYSIS OF AN ENDOCARDIAC SIGNAL OF ACCELERATION

CROSS-REFERENCE TO RELATED PATENT APPLICATIONS

This application is a continuation of U.S. patent application Ser. No. 12/389,291 filed Feb. 19, 2009, which claims priority to France Priority Application 08-00907, filed Feb. 20, 2008 including the specification, drawings, claims and abstract, both of which are incorporated herein by reference in their entireties.

BACKGROUND OF THE INVENTION

The present invention relates to the processing and analyzing of endocardiac acceleration signals for use in the diagnosis of a patient condition and the control of an active medical device, and more particularly for the evaluation of the effectiveness, and the search for optimal configuration, of an active medical device implementing a technique known as CRT (Cardiac Resynchronization Therapy) or BVP (Bi-Ventricular Pacing).

In the particular case of CRT devices, an apparatus is implanted within a patient that is provided with electrodes that allow for stimulating the ventricles. The device is able to monitor the cardiac rhythm and to deliver, if necessary, electric impulses to stimulate the left ventricle and right ventricle in order to resynchronize them. For this purpose, the device applies between the two ventricular stimulations a variable intra-ventricular delay, which may be positive or negative, and is adjusted so as to resynchronize the contraction of the ventricles with fine optimization of the hemodynamic state of the patient. One such CRT device is described, for example, in EP 1 108 446 A1 and its corresponding U.S. Patent Publication U.S. Pat. No. 6,556,866 (ELA Medical).

It is essential, in the implementation of such a therapy in patients suffering from cardiac insufficiency or failure, to evaluate the effectiveness of the therapy in order to appreciate the relevance of it, and in the affirmative to maintain its effectiveness by modifying as needed the operation parameters of the implanted device.

The specific parameters of the CRT stimulation are generally represented by a "stimulation configuration", which is a combination of the characteristics relative to the "stimulation sites" and of the characteristics relative to the "stimulation sequence". The "stimulation sites" refer to the physical location of the intracardiac electrodes in relation to myocardium tissue. These sites can be selected at the time of the implantation by a suitable positioning of the electrodes. In the case of the prostheses known as "multisite" where the device comprises several electrodes placed in the same cardiac cavity, the modification of the stimulation site in this one cavity is also possible by an internal commutation of the device that selects one or more electrodes positioned at different locations on the myocardium. The concept of "stimulation sequence" refers on the one hand to the order in which the stimulation impulses are applied to the heart (e.g., atrium/left ventricle/right ventricle), and on the other hand to the time intervals separating the application of these successive impulses. Here still, the stimulation sequence is parameterized at implantation time, but can be modified thereafter by selecting the internal commutations of the device and by adjustment of the sequencing parameters of the stimulation impulses.

It is necessary to regularly evaluate the relevance of the stimulation configuration, because it conditions the effectiveness of the therapy with bi-ventricular pacing. Moreover, the beneficial effects provided by this therapy can result, in the long term, in revaluing the initial configuration for modifying eventually the choice of the sites and/or the pacing sequence parameters.

One of the known practices used to optimize the pacing parameters concerns estimating the characteristic delays of the systole, in particular the time of opening of the aortic valve, by an echographic evaluation. This procedure, which must be implemented in hospital by qualified personnel, is long and expensive and cannot be applied as often as it would be useful or necessary, without interfering with the daily life of the patient.

Another solution, suggested by the above mentioned EP 0 108 446 A1, concerns evaluating the degree of synchronization of the contractions of the ventricles by a measurement of intracardiac bio-impedance, this data being indeed representative of the cardiac flow and thus of the fraction of ejection, considered as a reference hemodynamic parameter.

The present invention is based on another approach to bi-ventricular stimulation, namely implementing an analysis of endocardiac acceleration (indicated hereafter as "EA"). Indeed, the clinical studies that were undertaken indicate that endocardiac acceleration is a parameter that makes it possible to provide very complete information about the functional state of the myocardium, as well in the case of a normal function and a defective operation: the endocardiac acceleration, which is measured by an accelerometer directly in contact with the cardiac muscle (generally, but not exclusively, with the ventricular right apex, sometimes with the right atrium), reflects indeed very precisely and in real-time the phenomena contributing to the mechanical functioning of the heart.

More precisely, the publication EP 0 515 319 A1 and its corresponding U.S. Pat. No. 5,304,208 (Sorin Biomedica Cardio SpA) teaches the method of collecting an endocardiac signal of acceleration by means of an endocavitary probe equipped with a pacing distal electrode implanted in the lower part of the ventricle and integrating a microaccelerometer that allows measuring an endocardiac acceleration. The endocardiac signal of acceleration collected (i.e., detected) during a cardiac cycle forms two principal components, corresponding to the two major sounds of the heart (S1 and S2 sounds of the phonocardiogram) which is possible to recognize in each cardiac cycle:

the first component of endocardiac acceleration ("EA1"), whose variations of amplitude are closely related to the variations of the pressure in the ventricle (the maximum peak-to-peak of this component EA1, called PEA1 amplitude, being more precisely correlated to the positive maximum of the variation of pressure dP/dt in the left ventricle) and can thus constitute a parameter representative of the contractility of the myocardium, itself related to the level of activity of the sympathetic nerve system; and the second endocardiac component of acceleration ("EA2") which occurs during the phase of isovolumic ventricular relaxation. This second component is produced, mainly, by the closing of the aortic and pulmonary valves.

The detected signal EA also may contain one or two other components, called EA3 and EA4, corresponding to the S3 and S4 sounds of the phonocardiogram. These sounds generally are the sign of a cardiac failure (EA3 being a priori due to the vibrations of the myocardium walls during a fast filling condition, and EA4 being due to the atrial contraction). The term "EAx component" will refer hereafter indifferently to one of the four EAx components, preferably, but not limited to, component EA1 or component EA2.

The EP 0 655 260 A1 and its counterpart U.S. Pat. No. 5,496,351 (Sorin Biomedica Cardio SpA) describes a manner of processing the signal of endocavitary acceleration delivered by the sensor located at the extremity of the probe and the method to derive from it two values related to the respective peaks of endocardiac acceleration. These values are useful in particular for the detection of cardiac disorders and the application or not of a defibrillation therapy.

The EP 1 736 203 A1 and its counterpart U.S. Patent Application Publication U.S. 20060293715 (ELA Medical) describes an application specific to bi-ventricular pacing implants, concerning using the parameters related to endocardiac acceleration to determine an optimal pacing configuration for the patient, at the time of the implantation or subsequently. Various measurements are taken to characterize the EA signal, and are combined to give a composite index of performance. The choice of the final pacing configuration is then one that which maximizes the index of performance.

U.S. Pat. No. 7,139,609 B1 refers to an implanted device that provides a follow-up of the cardiac function starting from an endocardiac acceleration signal, to optimize the general operation of a pacemaker or to apply a ventricular resynchronization therapy. Each cardiac cycle is analyzed to identify the two major sounds and to analyze the signal in order to deduct some from the parameters such as dP/dt, ejection volume, etc.

The EP 1 741 387 A1 refers to a diagnosis technique of measuring the peak-to-peak amplitude of EA1 (called PEA1) and/or the peak-to-peak amplitude of EA2 (called PEA2) during several successive cycles, and from this to analyze the variations of the detected amplitude to detect a situation of apnea or of hypopnea, and to deliver a suitable alarm.

It will be noted that although the present description refers mainly to the analysis of a signal EA delivered by an implanted sensor (typically, a sensor placed on a endocavitary probe), the invention is equally applicable to an analysis that is carried out using an external signal EA obtained in a noninvasive manner. Such an external signal EA can result, for example, from a sensor fixed on the chest of the patient at the level of the sternum, the ECG signal being simultaneously collected by means of external electrodes and being recorded. Thus, it should be understood that the term "signal EA" means and includes either an external signal EA, obtained noninvasively, or an endocavitary signal EA, obtained by an acceleration sensor mounted on a probe implanted in direct contact with the myocardium of the patient. In the latter case, the implanted device also typically will acquire an electrogram signal EMG that is simultaneously recorded with the endocavitary signal EA.

SUMMARY OF THE INVENTION

It is therefore, an object of the present invention to propose a device implementing a sophisticated technique for the analysis of signal EA in order to be able to extract from it a certain number of significant pieces of information, representative of the mechanical and hemodynamic activity of the heart of the patient, with in particular the elimination of the influence of the variations cycle-to-cycle of signal EA, which variations are likely to distort the results delivered by the algorithm employed to analyze the signal EA.

It is another object of the present invention to propose a device implementing a technique for analyzing the signal EA which also takes account the specificity of each of the EAx components, preferably the two components EA1 and EA2, separately considered.

It should be understood, however, that the present invention is not limited to the analysis of only the components EA1 and EA2 (whether these components are considered individually or jointly). Indeed, in the alternative or in complement, the present invention is applicable in a comparable manner to the analysis of components EA3 and/or EA4 associated with the S3 and S4 sounds of the phonocardiogram. For purposes of clarity, the following discussion will generally refer to components "EA1" or "EA2", but it should be understood that the discussion concerning components "EA1" or "EA2" must be regarded as applicable mutatis-mutandis to components EA3 and/or EA4.

In a general way, one of the goals of the invention is to propose a novel method of analysis of signal EA making it possible to increase the specificity and the relevance of the results provided by the algorithm for analyzing signal EA, particularly in order to obtain characteristics correlated to the temporal markers of the systole ("timings" of the cardiac cycle) and to other indices of the hemodynamic performance of the myocardium. In this regard, the evolution of the characteristics thus extracted, beat after beat, are evaluated so as to be able at each moment to consider the hemodynamic performances of the heart and to thus deliver an optimal ventricular resynchronization therapy for the patient. This estimate of hemodynamic performance must in particular be able to take into account the evolution of the optimal stimulation configuration through time, as this configuration can be different in a state of rest and in a state of effort. Heretofore, the stimulation configuration has been optimized at rest only.

In addition to the automatic optimization of the therapy, the analysis of signal EA can provide valuable indications in particular for:

the guidance of the probe at the time of the implantation, starting from certain preselected characteristics of EA;
the localization of the optimal pacing site (position of the left or right probe);
the diagnosis of the health condition of the patient, by a permanent follow-up of the risk of cardiac failure;
the discrimination of arrhythmias;
the impact of events such as apnea, arrhythmia, etc on the hemodynamic state of the patient.

Broadly, the present invention is directed to a device for analyzing an endocardiac acceleration signal EA employing a processor with control software, logic and associated digital circuitry to receive an input signal EA corresponding to a plurality of cardiac cycles, and after processing produces an output of at least one characteristic data correlated to temporal parameters at least one cardiac cycle and/or to the hemodynamic performances of the myocardium. The device in accordance with the present invention comprises the improvement wherein the input signal EA is preprocessed by performing the following functions:

the input signal EA is cut (or separated) into a sequence of a plurality of isolated EA signal segments, by determining markers corresponding to a beginning of a cardiac cycle, thereby isolating the successive cardiac cycles in this sequence, so as to produce a series of sub-signals EA, each one having a duration of one cardiac cycle;
each of the series of sub-signals EA is separated out and has isolated in it at least one component EAx that is associated with one of the heart sounds S1, S2, S3, and S4; and
a correlation is then performed, operating on the at least one isolated component EAx, to seek a degree of correlation, preferably a maximum of correlation, and operate a relative temporal retiming of each of the sub-signals EA compared to the maximum, so as to deliver a readjusted component EAx associated with each sub-signal EA.

It should be understood that the maximum of correlation is believed by the inventors to be useful for carrying out the readjustment of the component EAx's in accordance with the present invention, and it is also believed that a degree of correlation less than the maximum also can be used to achieve the readjustment, which degree of correlation can be determined by a person of ordinary skill in the art, to provide a reference for isolating each component EAx in each sub-signal EA to permit the temporal retiming of each of the sub-signals EA.

In addition, the device of the present invention preferably also analyzes the signal by:

isolating in each of the sub-signals EA a component EA1 associated with the first cardiac major sound S1 for said sub-signal, and a component EA2 associated with the second cardiac major sound S2 for the same sub-signal; and correlating each said isolated component EA1 and EA2, to seek a maximum of correlation, performing a relative temporal retiming of each isolated sub-signal relative to said maximum, and delivering a readjusted component EA1 and a readjusted component EA2 associated with each sub-signal of the aforesaid series of sub-signals EA.

Further, the device preferably next analyzes the signal EA by determining, in response to said readjusted components EA1 and EA2, an average component EA1 and an average component EA2, and for combining said average components EA1 and EA2 so as to produce an average global signal EA on a cycle.

In another preferred embodiment, the device of the present invention processes the signal EA by determining temporal markers of characteristic moments in the cardiac cycle, starting from the aforementioned average global signal EA for a cycle delivered by a preprocessing function. More preferably, the temporal markers are correlated to the moments of opening and closing of the aortic, mitral, pulmonary and/or tricuspid valves.

Optionally, the cutting of the signal EA is performed by calculating a median or average duration of the cycles of the sequence of cardiac cycles, and adjusting the duration of each sub-signal EA at a same duration corresponding to said determined median or average duration.

Yet another embodiment of the device provides for a means for calculating a value of the difference in the amplitude peak-to-peak of the endocardiac acceleration for the components EA1 or EA2 respectively (peaks "PEA1" or "PEA2" respectively) by operation on each component EA1 and EA2. In addition, the device may include means for calculating a value of entropy of the component EA1 or EA2, said means operating in a distinct way on each of components EA1 and EA2. Another feature of the device of the present invention allows for calculating one of an Shannon energy envelope or an envelope based on homomorphic filtering, applied to that average global signal EA averaged on a cycle. The processing function also can include estimating an instantaneous fundamental frequency of the aforementioned average global signal EA for a cycle by application of an estimated autoregressive model in a recursive manner. Indeed, in one such embodiment, the device can include a means for detecting a characteristic data selected from among the group consisting of: a moment of rupture of the frequency, a moment of inflection of the frequency, a moment of maximum frequency, and a non temporal data determined starting from estimated models of variation of the frequency over time.

In one aspect of the invention, the device preferably controls an automatic selection of at least one of a plurality of different processing algorithms according to criteria applied to said average component EA1 and/or said average component EA2. The results of the different processing algorithms, when performed jointly, can be combined in a linear or non-linear manner, for at least one of the aforesaid data characteristic correlated to temporal parameters of the cardiac cycle and/or to the hemodynamic performances of the myocardium.

Another aspect of the invention contemplates use the aforementioned device together with means for determining, starting from a determined average global signal EA for a cycle, at least one parameter selected from among the group consisting of: a variability cycle-to-cycle of temporal markers corresponding to a characteristic moment in the cardiac cycle, a median frequency of the signal in predetermined intervals, an accumulated energy of the signal in predetermined intervals, and a maximum energy of the signal in predetermined intervals. Another feature that may be employed with the device is a means for calculating a value of signal/noise ratio of the at least one EAx component, more preferably the components EA1 or EA2 respectively, said means operating in a distinct way on each of components EA1 and EA2. Further, the device may include means for detecting a presence of ectopic beats in said sequence of cardiac cycles, and for eliminating said sub-signals EA relative to those cardiac cycles affected by said detected ectopic beats.

Optionally, the device may employ a monitoring mode of follow-up of the temporal evolution of the characteristics of the signal EA on a sliding window of analysis extending over at least one cardiac beat. In addition, statistics may be calculated on the temporal markers, said calculations of characteristics being extracted at various successive moments throughout the detected signal EA. It should be understood that conventional microprocessor-based computing systems can be used, with memory and registers for processing the acquired EA signal and manipulation of the data detected, under the control of software that provides instructions for performing the various functions and process steps disclosed herein. Such microprocessor based systems are found in any of a number of active medical devices and may be adapted by programming with suitable software that can be developed by a person of ordinary skill in the art.

BRIEF DESCRIPTION OF THE DRAWINGS

Further features, advantages and characteristics of the present invention will now be described in connection with the following detailed discussion of preferred embodiments of the invention, made with reference to the annexed drawings, in which the same numerical references indicate, from one figure to another, identical or functionally similar elements, and in which:

FIG. 1 is a series of three chronograms illustrating various signals characterizing the cardiac activity during a given cycle;

FIG. 2 is a general flowchart of the various stages for analyzing signal EA in accordance with a preferred embodiment of the present invention;

FIG. 3 illustrates cutting a continuous recording in a series of successive cardiac cycles;

FIG. 4 illustrates an extraction of components EA1 and EA2 on a 'sub-signal' EA;

FIG. 5 illustrates an example of calculation of intercorrelation functions between two sub-signals, to readjust the components of the various successive cycles;

FIG. 6 illustrates the generation of an average cycle starting from the pretreated data for each of two components EA1 and EA2;

FIG. 7 illustrates two examples of components EA1 for two different signals, one presenting a low value of contrast and the other a high value of contrast;

FIGS. 8, 9a and 9b illustrate the stage of processing involving calculation of a Shannon energy envelope;

FIG. 10 illustrates the stage of processing involving application of an autoregressive model estimated in a recursive manner; and FIG. 11 illustrates the stage of calculation of a value of signal-to-noise ratio, applied to component EA2.

DETAILED DESCRIPTION OF THE PREFERRED EMBODIMENTS

With reference to the drawings, FIG. 1 illustrates the various signals characterizing the activity of the heart during a cardiac cycle, with: the intracardiac pressures profile ($P_A$, $P_{VG}$ and $Po_G$), a recording of the surface electrocardiogram (ECG), and the variations of the endocardiac acceleration signal (EA).

The characteristic $P_A$ illustrates the variations of the aortic pressure, $P_{VG}$ those of the left ventricle and $P_{OG}$ those in the left atrium. The points A to E correspond to the various following phases: A—contraction of the left atrium, B—closing of the mitral valve, C—opening of the aortic valve, D—closing of the aortic valve, E—opening of the mitral valve.

The ECG signal presents successively the P-wave corresponding to the depolarization of the atria, the QRS complex corresponding to the depolarization of the ventricles, and the T-wave corresponding to the ventricular repolarization.

The endocardiac acceleration signal EA can be divided into two successive components: the component EA1, which begins following the QRS complex, is generated by a combination of the closing of the atrio-ventricular valves, opening of the semilunar valves and contraction of the left ventricle, and the component EA2, which follows relates to the end of the ventricular systole, is generated by the closing of the semilunar valves. These two components EA1 and EA2 correspond classically, as indicated above, to the two principal cardiac sounds S1 and S2.

Primarily, the present invention proposes to extract from the acceleration signal and more precisely from at least one component EAx, and more preferably from the two components EA1 and EA2 (and/or EA3 and EA4) by a specific processing of each one of them, characteristics correlated to time intervals of the systole and to other indices of hemodynamic performance of the myocardium.

The general sequence of the analyzing process according to the invention is illustrated by the flow chart in FIG. 2. This analysis of signal EA requires the acquisition of a minimum of N successive cardiac beats. The analysis can be operated:

either in a "monitoring" mode, using an analysis sliding window of N beats (N≥1), to follow the temporal evolution of the various characteristics of signal EA (in this case N=5, typically), or in a "sweeping of the configurations" mode, for a plurality of recordings of N successive beats acquired with various stimulus configurations under stable conditions, so as to determine the optimal stimulation configuration according to a certain number of predetermined criteria (in this case N=5, typically).

The acquisition of signal EA can be made, as noted, by an implanted prosthesis equipped with an adapted sensor, for example, an acceleration sensor at the extremity of probe, or an external sensor applied to the thorax of the patient and collecting the sounds of the heart, for example, during an effort test. With reference to FIG. 2, the first stage 100 of the process concerns operating a cutting of the uninterrupted signal EA collected over N successive beats, preferably filtered beforehand by a band-pass filter, into individual segments of a continuous signal corresponding to the various successive cardiac cycles.

As illustrated in FIG. 3, defining the successive cardiac cycles C1, C2, C3 . . . from the continuous signal EA may be obtained by determining the markers of the beginning of a cycle, thereby making it possible to individualize these cardiac cycles, so as to produce a series of sub-signals EA corresponding each one to the duration of only one cardiac cycle:

in the case of an endocavitary signal EA, the temporal markers of beginning of cycle are provided by the implant itself, which keeps in memory the moments of stimulation V (as illustrated in FIG. 3) or the moments of detection of the R-wave, according to its operating mode;

in the case of an external signal EA, the temporal markers of cardiac beginning of cycle are provided by an algorithm of detection of the peaks of stimulation or the QRS complexes of the ECG signal, signal collected in addition by means of external electrodes.

Advantageously, the analysis also implements an algorithm for detecting ectopic beats, in itself known, making it possible in such a case to eliminate the cardiac cycles affected by the detected ectopic beats, namely: the cycle preceding the ectopic beat, the cycle including the ectopic beat itself, as well as the cycle following the ectopic beat.

The various sub-signals EA, each one corresponding to one duration of a cardiac cycle, are thus individualized and then analyzed so as to determine an average length of cycle, and more preferably a median length, for the N successive beats. The algorithm then operates a re-analyzing of the continuous signal EA, so as to define sub-signals EA readjusted over this same common median length. This technique makes it possible in particular to avoid situations in which a stimulation peak would not have been detected, which would have given an affected sub-signal EA a duration approximately double that of its real duration. After this adjustment of duration, one obtains a matrix made up of N sub-signals EA, all having the same duration, a duration equal to the calculated median duration.

The following stage 110 (FIG. 2), concerns isolating two components EA1 and EA2 in each sub-signal EA, so as then to be able to carry out a certain number of processing steps in a distinct way for each one of these components EA1 and EA2. The extraction of two components EA1 and EA2 is operated by a correlation technique applied to the N sub-signals EA obtained in the way indicated above.

FIG. 4 illustrates the two windows of useful signals EA1 and EA2, obtained by exploiting the reproducibility of two components EA1 and EA2 on the N sub-signals EA. The duration of each one of these two windows can be a fixed duration, or eventually a variable duration, in particular a duration that is a function of a percentage of interval RR, so as to allow a better adaptation to the case of the fast rhythms. It will be noted that these two windows can be partially overlapping, or not as the case may be. Starting from the matrix of the N sub-signals EA, one thus obtains two independent matrices containing respectively components EA1 and EA2 of the N analyzed cardiac cycles.

The following stage, referenced 120 or 120' on FIG. 2, concerns operating a temporal retiming of the N cycles, distinctly and in parallel for each of two components EAx (EA1 and EA2). A first technique involves, for each pair of sub-signals of the matrix, seeking the maximum of the standardized intercorrelation function, a function that will vary between 1 (in the case of two perfectly correlated vectors) and 0 (in the case of two uncorrelated vectors):

$$\Gamma_{i,j}(\tau) = \frac{\sum_{t=0}^{Nsamples-1}(ea\_cycles_i(t+\tau)-\mu_{ea\_cycles_i}) \cdot (ea\_cycles_j(t)-\mu_{ea\_cycles_j})}{\sqrt{\sum_{t=0}^{Nsamples-1}(ea\_cycles_i(t)-\mu_{ea\_cycles_i})^2 \cdot \sum_{t=0}^{Nsamples-1}(ea\_cycles_j(t)-\mu_{ea\_cycles_j})^2}}$$

In this expression, i or j=1 or 2, $ea\_cycles_1(t)$ and $ea\_cycles_2(t)$ represents the terms of the matrices of the N sub-signals of the respective considered component, EA1 or EA2 (the same processing is operated for each of the two components).

The result, illustrated in FIG. 5, is a pair of analyzed sub-signals in FIG. 5a and the corresponding function of intercorrelation in FIG. 5b. With reference to the example illustrated in FIG. 5, the maximum of the function of intercorrelation is at r=−5 samples, with a value of peak of 0.78. That means that by delaying $ea\_cycles_1(t)$ of 5 samples, $ea\_cycles_1(t)$ and $ea\_cycles_2(t)$ is correlated to r=0.78.

Two tables then are built: one containing the coefficients of correlation $r_o$ of the various pairs, the other one containing the delays $r_{i,j}$, allowing to readjust the various sub-signals $ea\_cycles_i(t)$ as compared to the others. One then locates that cycle best correlated to the other $ea\_cycles_i(t)$ (i≠j) by calculating for each i the average coefficient of correlation with the other sub-signals.

The sub-signal of reference will be that presenting the maximum average coefficient of correlation: reference_cycle_ind_EAx. Then the sub-signals are retained $ea\_cycles_j(t)$ (with j≠reference_cycle_ind_EAx) which answers the two following criteria:

$r_{reference\_cycle\_ind\_EAx,j}$>threshold of EAx correlation, and $|\tau_{reference\_cycle\_ind\_EAx,j}|$>threshold of time of correlation.

On the N initial sub-signals, there remain N' EAx cycles after this stage of selection. By keeping only the indices j of the selected cycles, one defines the Ax_correlation=average ($r_{reference\_cycle\_ind\_EAx,j}$) (with j≠reference_cycle_ind_EAx).

An alternative embodiment of the process of the present invention, one that is less demanding in terms of computing resources but also less robust, involves fixing the cycle of reference before calculating the correlations. This choice can be manual or at random, or fixed (for example, the first detected cycle), which significantly decreases the number of combinations to be analyzed, the remainder of the method being identical.

Another alternative of implementing this process, also demanding less computing time but less robust, relates to readjusting the N cycles compared to the moment tPEAx of arrival of the amplitude peak to peak of the EAx component of each cycle:

$t_{PEAx}$0.5×[t_min(EAx)+t_max(EAx)].

The shifts $\tau_{i,j}$ between each pair of cycles are calculated so that these moments of peak to peak amplitude are synchronous. It is enough to calculate a coefficient of correlation only for this value of shift, which significantly decreases the number of operations to be realized, the remainder of the method being identical.

Another alternative still, one particularly advantageous of terms of software resources, involves operating a detection of the peaks in accordance with an algorithm in meta language such as this one:

For each EAx cycle:
Locate the peak of the maximum, in absolute value, inside the window;
Open a window around this peak (beginning, for example, 100 ms before the maximum and finishing 100 ms after, this parameter being eventually adjustable by programming);
Locate two local extrema inside this window, if required with addition of an additional condition on the second derivative (by testing the value of sample i with that of the samples i+2 and i−2) to discriminate a particular type of extremum, and preserve the three extrema having the largest absolute amplitudes; if there is no other extremum apart of the peak, preserve only the peak;
Then, between EAx of reference and each one of other EAx of the window of analysis:
calculate all the possible inter-extrema distances;
select the two closest peaks, which will be regarded as peaks of reference;
calculate the temporal interval τ between these two peaks of reference;
readjust τ the cardiac cycle running compared to the cycle of reference; calculate the standardized coefficient of correlation r, for this value of τ only.

It will be noted finally that it is possible to combine any of the four methods different of retiming described above.

In the case of a sliding analysis (a "monitoring" function) it will be enough to eliminate the first cycle in conformity, and to operate the analysis with the next detected cycle. If this next cycle satisfies the conditions of correlation, this cycle is added to the cycle in conformity, if not, an analysis is carried out on the following cycle. If however it is not possible to check these conditions after five successive cycles, it will be considered that corresponding component EA1 or EA2 is not reproducible from one cycle to another. If, in the "monitoring" mode, the number of beats to be used for the sliding window of analysis is 1, this stage of preprocessing will not be applied, and one will pass directly to block 140 in FIG. 2.

At this stage, it is possible to apply an algorithm that is a "rejector" of artifacts. This algorithm can be in particular based on the calculation of the one of the following quantities, with the choice:

$$\mu^i_{EAx\_window} = \frac{1}{N_{EAx\_window}} \cdot \sum_{t \in EAX\_window}(ea\_cycles_i(t))$$

$$\sigma^i_{EAx\_window} = \sqrt{\frac{1}{N_{EAx\_window}} \cdot \sum_{t \in EAX\_window}(ea\_cycles_i(t)-\mu^i_{EAx\_window})^2}$$

$$B_i = \sum_{t \in EAX\_window}(ea\_cycles_i(t))^2$$

$N_{EAx\_window}$ being the number of samples in the EAx_window window.

The algorithm calculates then the average $\mu_{CRIT\_ARTEFACT}$ and the standard deviation $\sigma_{CRIT\_ARTEFACT}$ of the chosen value, on the whole of the N EAx cycles. One can then choose to select only components i such as $|CRIT\_ARTEFACT(i)-\mu_{CRIT\_ARTEFACT}|<\alpha \cdot \sigma_{CRIT\_ARTEFACT}$, $\alpha$ being a variable coefficient (typically equal to 2).

The following stage, corresponding to block 130 in FIG. 2, concerns defining an average cycle starting from components EA1 and EA2, separately pretreated in the manner indicated above. For this purpose, sub-signals EA1 and EA2 of each cycle are readjusted compared to the sub-signal of reference reference_cycle_ind_EAx. One starts by centering the values $\tau_{reference\_cycle\_ind\_EAx,j}$ calculated at the precedent stage by subtracting the median value $\tau_{reference\_cycle\_ind\_EAx,j}$ for all of the j values (including the cycle of reference). One then uses these new values $\tau_{reference\_cycle\_ind\_EAx,j}$ to readjust sub-signals EA1 and EA2 compared to the sub-signal of reference $\tau_{reference\_cycle\_ind\_EAx,j}$. Once the sub-signals are readjusted, it is enough to calculate an average component EA1 or EA2 and to form thus the average signal EA by combination of the two components. This average signal EA is illustrated FIG. 6a.

If one of two components EA1 or EA2 did not satisfy a condition Ncycles EAx>NcyclesEAx_min, an average global cycle is formed, by replacing the component in question by a zero value. This case is illustrated in FIG. 6b, if component EA1 would not answer the criteria.

At this stage, once the average cycle has been determined, it is possible to apply eventually a weighting factor to it in order to attenuate certain components which one knows the relative position in the cardiac cycle. For example, it is known that component EA4 occurs between the beginning of the atrial electric activity (the P-wave in the case of an ECG, or the detection of the depolarization on the atrial probe in the case of an implantable device) and the beginning of component EA1. If one wants to prevent component EA4 from disturbing the following stages of the processing, one will be able to apply a weight function built starting from a form window of a selected duration and position. This weighting window can for example be a Hamming window with a 75 ms duration with a temporal position of the minimum of the weight function at 0 ms.

The following stage, corresponding to block 140 in FIG. 2, performs calculating contrast and entropy values for each component EA1 and EA2. The value of contrast is calculated by determining the amplitude peak-to-peak of the average cycle EA on the considered window. The contrast of the EAx component is given by a formula such as:

$$\text{contrast\_EAx} = \frac{PEAx}{2 \cdot \sigma_{EAx\_window}}$$

A high value of contrast means that the useful component EAx is localized in time. On the contrary, a lower value of contrast corresponds to a spreading out much more important of the EAx component. These two situations are illustrated for the examples of the FIG. 7a (low value of contrast) and 7b (correct value of contrast).

One defines on the same analysis windows a value of entropy given by a formula such as:

$$\text{entropy\_EAx} = -\sum_{EAx\_window} (average\_ea\_cycles_i(t) \cdot \log 10 (average\_ea\_cycles_i(t)))$$

This quantity reflects the "degree of order" of the signal: if the signal is close to a white noise the entropy will be raised, if on the contrary it "is ordered", the entropy is lower.

It is at this stage possible to evaluate an index of morphology of components EA1 and/or EA2 which can be correlated to indices of performances of the heart, or which can be used to choose such or such version of algorithm, better adapted to a certain morphology. For this, the device determines an energy curve envelope by one of the following described methods, and then calculates for each EAx component the surface under this curve: the index of morphology is then given by the reverse of this surface.

Also at this stage, it is possible to operate a low-pass, high-pass, band pass filtering or an adaptive filtering of the average signal EA before the generation of the envelope, for example, a high-pass filtering on 128 samples at 25 Hz.

It is possible to use for these purpose filters of the type 'finished impulse response' (FIR) or the filters of the type 'infinite impulse response (IIR)'. One can choose to filter in the direction of the unfolding of the samples, or to filter in this direction then to filter with the same filter the output of this filter in the opposed direction, in order to compensate for the dephasing induced by the filtering.

An adaptive filtering can be also carried out on the average signal EA before any other processing, by a filter such as:

$$y(nT) = \hat{n}_1(nT) = \sum_{k=0}^{P} w_{k,nT} x_2(nT - kT)$$

y(NT) being the output of the adaptive filter,
x2 (NT) being the signal of reference, and
wk, NT being the coefficients of the filter, which will be learned in an adaptive way.

An algorithm LMS (Least Mean Squares) can be used to learn the coefficients of the filter in the following way:

$$w_n = w_{n-1} + 2\mu(x_1(nT) - y(nT))x_2(nT)$$

x1 (NT) being the signal to be treated, here the average signal EA.

This adaptive filtering is particularly useful to separate the component EA4 which can be superimposed on component EA1, thus guaranteeing a better processing of the filtered signal EA1.

In this last case, the signal x2 (NT) will be the atrial activation time (determined by a processing of a surface signal ECG or of a signal EGM), and the learning of the coefficients of the filter will be able to have a value of μ that is a function of the atrio-ventricular delay (AV delay) observed or imposed by the device, for example μ=0 for short AV delays (during the superposition of EA4 on EA1) and μ>0 for long AV delays (when EA4 and EA1 are not superimposed).

The stage of adaptive filtering could be also used to cancel the 50/60 Hz noise in the case of an external acquisition (thoracic sensor). This adaptive filtering also can be used to isolate the component EA4 in the signal and allow a separate analysis of this component, preferably for a diagnostic use (and the same is true for component EA3).

In the case that the adaptive filtering is used, following it the average signal EA is then subjected to a global analysis, i.e. this analysis is carried out on the average signal EA for a duration corresponding to a cardiac cycle, without operating a differentiated processing on two components EA1 and EA2 (with the difference in the stages of preprocessing described above).

Advantageously, the algorithm can implement several different methods of analysis (blocks 160, 160' and 160" on FIG. 2), the choice of the method being operated (block 150 on FIG. 2) according to the results of the aforementioned preprocessing.

It is thus possible to have a method of analysis (hereafter "method of segmentation") in comparison to the others, for example, if the preprocessing revealed a good correlation of components EA1 and/or EA2. It is also possible to combine the results of several methods of segmentation, or to not start any analysis, for example, if it is considered that one and/or the other of components EA1 or EA2 takes a too chaotic form (according in particular to the values of contrast and entropy calculated at the preceding stage).

A first method of segmentation (block 160' on FIG. 2), in itself known, is based on calculation of an energy envelope, according to the following generic formula:

$$nrg(t) = \sum_{u=t-h\_nrg/2}^{t+h\_nrg/2} Fenetre(u) \times F(\text{average\_ea\_cycle}(u))$$

Fenetre (u) being a weighting window of width h_nrg (rectangle, the Hamming window or another window of weighting) in order to smooth more or less the edges effects. F is a function that is applied to the samples average_ea_cycle(u) which can be an unspecified function (linear or non-linear), for example: the transform of Shannon, a polynomial function, or an 'absolute value' function.

It is also possible, if necessary, to subsample the envelope of energy obtained.

FIG. 8 illustrates, on the same chronogram, the average cycle EA and the energy envelope of Shannon EESh thus calculated.

On the considered window of analysis EA1 or EA2, the algorithm seeks the maximum amplitude of the energy envelope, and preserves its value and the associated temporal markers (stored in memory). The algorithm then seeks the first sample of the energy envelope preceding the maximum, and whose value is equal to a given threshold S (which may be a percentage of this maximum, or a particular value). This makes it possible to detect the going-up front of the envelope and to define a temporal marker T1, as illustrated in FIG. 9a. In the same way, for the posterior part to the maximum, the crossing of the threshold defines a second temporal marker T2 of end of the envelope of energy of the average cycle EA.

One will note that the thresholding can take into account other parameters and criteria, in particular to take into account the temporal difference between T1 and T2, to envisage the multiple cases of crossings of the threshold resulting from "double bump" profiles, etc.

For example, as illustrated FIG. 9b, a case is shown where the curve representative of the envelope crosses the threshold S four times, in t1, t2, t3 and t4. Various approaches are possible with regard to such a situation:

- to retain t1 and t4, two extreme points;
- to retain t1 and t2, points relating to the energy component (Maxi>Max2);
- to retain t3 and t4, points relating to the energy component (Max2<Max1);
- to choose which points of beginning and end will be retained, according to minima and maximum thresholds, for example:

ti and tj so that $|tj-ti|>\Delta min$ and $|tj-ti|=\min(|tx-ty|)$ $(x \neq y)$ $t_j$ and $t_i$, so that $|t_j-t_i|<\Delta min$ and $|t_j-t_i|=\min(|t_x-t_y|)$ $(x \neq y)$ A second method of segmentation (block 160' on FIG. 2) is that of the homomorphic envelope. It is implemented with application of a low-pass filter making it possible to eliminate the component from frequency modulation, typical component of the fast variations which one seeks to eliminate. The component in amplitude modulation obtained after this filtering, called "homomorphic envelogramme" is treated in a way comparable with the preceding method, to determine markers T1 of beginning and T2 of end of the envelope of energy of the average cycle EA.

A third technique of segmentation, (block 160" shown in FIG. 2) concerns applying a recursive autoregression model (RAR). The idea here is to consider at every moment the fundamental frequency of the signal EA, by analyzing the phase of the poles of an autoregression model estimated in a recursive way (with a criterion of elimination of error RLS, Recursive Least Square); this algorithm is also known under the name of "forgetting Factor approach".

For this purpose, for each sample of the signal at the input the algorithm considers a autoregression model of order 2 by considering a certain segment of the signal preceding this sample (a segment of width adjustable by the parameter "forgetting Factor"), according to the following formula, where X is the vector entry signal and where N=2 in this case:

$$x[n] = -\sum_{k=1}^{N} a_n x[n-k] + v[n]$$

The first term corresponds to the linear prediction, and the second with the error of prediction:

$y\Sigma w_k x_k + \epsilon$

This equation can be put in the form of an autoregressive model:

$$H(z) = \frac{1}{1 + \sum_{k=1}^{N} a_k z^{-k}} \Rightarrow P(\omega) = \frac{\sigma_v^2}{\left|1 + \sum_{k=1}^{N} a_k e^{-j\omega k}\right|^2}$$

It is possible to calculate the poles of the model by solution of a second order equation. By calculating the phase of these poles, one obtains an estimate of the instantaneous frequency of the entry signal:

$$freq(t) = \frac{\text{phase(poles)} \cdot fs}{2\pi}$$

"Forgetting Factor" rar_ff is a very important parameter, which makes it possible to set the sensitivity of the algorithm for the abrupt changes of frequency, and thus for the noise. This parameter can also be expressed by the concept of "memory horizon":

$$rar\_ff = \frac{1}{1-rar\_memory\_horizon \cdot fs}$$

A long parameter "memory horizon" indicates a low sensitivity to the noise, with a long response time of the estimation. Conversely, a short parameter indicates a large sensitivity to the noise with a short response time.

One will note that, although RAR method is in itself known, it was improved, within the framework of this invention, by:

an additional preprocessing, by adding to the entry signal a white noise of variable variance, and
a median filtering on a certain number of samples of the signal of the obtained frequency.

This makes it possible to fix the algorithm only over the useful periods, as shown in the FIG. 10: in FIG. 10a is illustrated the average signal EA object of the processing, in FIG. 10b is illustrated the signal of raw estimated frequency, and in FIG. 10c is illustrated the median filtered signal finally obtained.

It is enough to put a threshold for this last signal with a fixed threshold to determine the markers T1 and T2 corresponding to the rising and downward fronts of each component EA1 and EA2.

Once the temporal markers are extracted from the average cycle by one and/or the other of the various methods of segmentation already described (blocks 160,160' and 160"), the following optional stage (block 170 on FIG. 2) makes it possible to return to temporal markers cycles to cycle, thanks to the values of the shifts calculated at stage 130. Indeed, the sub-signals selected with this stage 130 were shifted compared to the sub-signal of reference. One can thus calculate each moment of beginning t_EAx_start_xxx(j) (with j=1 ... NcyclesEAx) by applying the following formula:

$$t\_EAx\_start_j = t\_EAx\_start\_av - \tau_{reference\_cycle\_ind\_EAx,j}$$

One can thus calculate a median value of the temporal markers, as well as a standard deviation to have an idea of variability cycle to cycle of these temporal markers on NcyclesEAx beats (by making the assumption that in mode "sweeping of the configurations", signal EA is stationary and that one can thus approximate the standard deviation of these temporal markers by the value of the standard deviation of $\tau_{i,j}$).

The temporal markers of end t_EAx_end_xxx are determined in a similar way.

In the particular case of the "monitoring" mode, optionally, one can calculate statistics on the temporal markers, and on other characteristics extracted at various successive moments throughout the signal. Further, one can extract, for each selected beat and each component EA1 and EA2 of signal EA, the values of amplitude peak to peak in the window determined by the two limits, values which will be indicated as PEA1 and PEA2. One can thus calculate a median value and a standard deviation of PEA1 and PEA2 on the whole of the values obtained on the selected beats.

In the case of the technique of segmentation based on an autoregressive recursive model RAR (block 160" on FIG. 2), it is possible to extract other interesting temporal markers: one can indeed detect a certain number of characteristic moments among which a moment of rupture of frequency or a moment of inflection of frequency, according to the technique used (value of transition between two frequential components EAx), and the moment of maximum frequency. One will be able also to extract nontemporal characteristics, by estimating for example models of variation of the frequency during time (hyperbolic model, sigmoid, polynomials of higher, exponential, linear by extract, etc) and to use the parameters of these models (coefficients, time-constants, amplitude and phase of the poles, etc) as characteristics of a EAx component.

Once the average signal EA is completely segmented (time of beginning and end of components EA1 and EA2) one can define for each component a signal/noise ratio SNR:

–SNR_EAx=PEAx/(2×σ–noise),

σ_noise being the standard deviation of the signal considered as "noise", i.e. the signal contained in the window of useful signal EAx, except for the segment corresponding to the EAx component itself. This situation is illustrated on FIG. 11 for component EA2, where one can see that the noise to be evaluated for the calculation ratio SNR is that of the signal contained in the window of useful signal EA2 except for the segment corresponding to component EA2, starting from of t_EA2_start to t_EA2_end. If the segmentation of component EA2 would have failed, it will be considered that the signal of the type "noise" is the entire signal contained in the useful window of signal EA2.

The characteristics thus obtained can be combined and used (blocks 180 and 190 on FIG. 2) for the evaluation of the hemodynamic cardiac function of the patient.

Indeed, the temporal marker of beginning associated with component EA1 is correlated to the moment of opening of the aortic valve, while the temporal marker of beginning associated with component EA2 is correlated to the moment of closing of the aortic valve. One can thus easily evaluate the period of ejection, by calculation of the interval separating these two markers.

One can use other characteristics of the signal or a combination of characteristics to evaluate other indices of the cardiac function. These characteristics make it possible to follow the evolution of very important hemodynamic parameters, usually measured by echocardiography or during invasive examinations (pressure measurement in the left ventricle). These indications can moreover make it possible to evaluate the quality of a resynchronization therapy delivered to the patient, the localization of a site for optimal stimulation, the adjustment of the intra-ventricular time, etc, as that was exposed to the beginning of this description.

It is also possible to establish linear or non linear models, learned on a population including patients with cardiac insufficiencies and/or healthy subjects. These models will allow, once the "timings" of the components EAx (temporal positions their characteristic moments) are determined, to estimate a value of valvular "timings", such as the moments of opening/closing of the aortic valve, and the moments of opening/closing of the mitral valve.

One skilled in the art will appreciate that the present invention can be practiced by other than the described embodiments, which are presented for purposes of illustration and not of limitation.

What is claimed is:

1. An implantable medical device comprising:
   a processor;
   an endocardial acceleration sensor; and
   a machine-readable storage medium having instructions stored thereon that, when executed by the processor, cause the processor to:
   divide an endocardial acceleration (EA) signal into a plurality of EA sub-signals, wherein the EA signal is collected over a plurality of cardiac cycles using the endocardial acceleration sensor, and wherein each of the plurality of EA sub-signals corresponds to a single cardiac cycle of the plurality of cardiac cycles;

identify, in each of the plurality of EA sub-signals, at least one signal component associated with a type of heart sound, wherein each signal component is associated with the cardiac cycle of its EA sub-signal;

extract a characteristic of the at least one signal component for two or more of the plurality of cycles;

calculate a correlation coefficient correlating the characteristic of the at least one signal component for a first cycle of the plurality of cycles to the characteristic of the at least one signal component for a second cycle of the plurality of cycles; and perform temporal retiming of the at least one signal component based on the calculated correlation coefficient to generate one or more adjusted signal components of the associated one or more EA sub-signals.

2. The device of claim 1, wherein the instructions are further configured to cause the processor to generate output characteristic data based on the one or more adjusted signal components, wherein the output characteristic data is correlated to a hemodynamic performance of a myocardium.

3. The device of claim 1, wherein the instructions are further configured to cause the processor to identify a plurality of markers within the EA signal, wherein the instructions are configured to cause the processor to divide the EA signal into the plurality of EA sub-signals based on the markers.

4. The device of claim 1, wherein said correlation coefficient further comprises a maximum average correlation coefficient, and wherein said temporal retiming is relative to said maximum average correlation coefficient.

5. The device of claim 4, wherein the instructions are configured to cause the processor to identify in each of the EA sub-signals an EA1 component associated with a first cardiac major sound S1 and an EA2 component associated with a second cardiac major sound S2, and wherein the instructions are further configured to cause the processor to:

extract the characteristic, distinctly and in parallel, for both of said EA1 and EA2 components for each of said plurality of cycles;

calculate the maximum average correlation coefficient for both said EA1 and EA2 components correlating said extracted characteristics of the first cycle of said plurality of cycles and said extracted characteristics of the second cycle of said plurality of cycles, for each of said EA1 and EA2 components respectively;

perform relative temporal retiming of each EA sub-signal relative to said respective maximum average correlation coefficient; and deliver a readjusted EA1 component and a readjusted EA2 component associated with the plurality of EA sub-signals.

6. The device of claim 5, wherein the instructions are configured to cause the processor to determine an average global EA signal for a cycle, in response to said readjusted EA1 and EA2 components, an average EA1 component and an average EA2 component, and combine said average EA1 and EA2 components so as to produce the average global EA signal for a cycle.

7. The device of claim 6, wherein the instructions are configured to cause the processor to determine temporal markers of characteristic moments in the cardiac cycle, starting from the aforementioned average global EA signal for a cycle.

8. The device of claim 7, wherein said temporal markers comprise temporal markers correlated to moments of opening and closing of aortic, mitral, pulmonary and/or tricuspid valves.

9. A method comprising:

collecting an endocardial acceleration (EA) signal over a plurality of cardiac cycles using an endocardial acceleration sensor of an implantable medical device;

dividing the EA signal into a plurality of EA sub-signals, wherein each of the plurality of EA sub-signals corresponds to a single cardiac cycle of the plurality of cardiac cycles;

identifying, in each of the plurality of EA sub-signals, at least one signal component associated with a type of heart sound, wherein each signal component is associated with the cardiac cycle of its EA sub-signal;

extracting a characteristic of the at least one signal component for two or more of the plurality of cycles;

calculating a correlation coefficient correlating the characteristic of the at least one signal component for a first cycle of the plurality of cycles to the characteristic of the at least one signal component for a second cycle of the plurality of cycles; and performing temporal retiming of the at least one signal component based on the calculated correlation coefficient to generate one or more adjusted signal components of the associated one or more EA sub-signals.

10. The method of claim 9, furthering comprising generating output characteristic data based on the one or more adjusted signal components, wherein the output characteristic data is correlated to a hemodynamic performance of a myocardium.

11. The method of claim 9, further comprising identifying a plurality of markers within the EA signal, wherein the instructions are configured to cause the processor to divide the EA signal into the plurality of EA sub-signals based on the markers.

12. The method of claim 9, wherein said correlation coefficient further comprises a maximum average correlation coefficient, and wherein said temporal retiming is relative to said maximum average correlation coefficient.

13. The method of claim 12, further comprising:

identifying, in each of the EA sub-signals, an EA1 component associated with a first cardiac major sound S1 and an EA2 component associated with a second cardiac major sound S2;

extracting the characteristic, distinctly and in parallel, for both of said EA1 and EA2 components for each of said plurality of cycles;

calculating the maximum average correlation coefficient for both said EA1 and EA2 components correlating said extracted characteristics of the first cycle of said plurality of cycles and said extracted characteristics of the second cycle of said plurality of cycles, for each of said EA1 and EA2 components respectively;

performing relative temporal retiming of each EA sub-signal relative to said respective maximum average correlation coefficient; and delivering a readjusted EA1 component and a readjusted EA2 component associated with the plurality of EA sub-signals.

14. The method of claim 13, further comprising determining an average global EA signal for a cycle, in response to said readjusted EA1 and EA2 components, and an average EA1 component and an average EA2 component, and combining said average EA1 and EA2 components so as to produce the average global EA signal for a cycle.

15. The method of claim 14, further comprising determining temporal markers of characteristic moments in the cardiac cycle, starting from the aforementioned average global EA signal for a cycle.

16. The method of claim 15, wherein said temporal markers comprise temporal markers correlated to moments of opening and closing of aortic, mitral, pulmonary and/or tricuspid valves.

17. A non-transitory machine-readable storage medium having instructions stored thereon that, when executed by a processor, cause the processor to perform operations comprising:
- collecting an endocardial acceleration (EA) signal over a plurality of cardiac cycles using an endocardial acceleration sensor of an implantable medical device;
- dividing the EA signal into a plurality of EA sub-signals, wherein each of the plurality of EA sub-signals corresponds to a single cardiac cycle of the plurality of cardiac cycles;
- identifying, in each of the plurality of EA sub-signals, at least one signal component associated with a type of heart sound, wherein each signal component is associated with the cardiac cycle of its EA sub-signal;
- extracting a characteristic of the at least one signal component for two or more of the plurality of cycles;
- calculating a correlation coefficient correlating the characteristic of the at least one signal component for a first cycle of the plurality of cycles to the characteristic of the at least one signal component for a second cycle of the plurality of cycles; and
- performing temporal retiming of the at least one signal component based on the calculated correlation coefficient to generate one or more adjusted signal components of the associated one or more EA sub-signals.

18. The non-transitory machine-readable storage medium of claim 17, wherein the operations further comprise identifying a plurality of markers within the EA signal, wherein the instructions are configured to cause the processor to divide the EA signal into the plurality of EA sub-signals based on the markers.

19. The non-transitory machine-readable storage medium of claim 17, wherein said correlation coefficient further comprises a maximum average correlation coefficient, and wherein said temporal retiming is relative to said maximum average correlation coefficient.

20. The non-transitory machine-readable storage medium of claim 19, wherein the operations further comprise:
- identifying, in each of the EA sub-signals, an EA1 component associated with a first cardiac major sound S1 and an EA2 component associated with a second cardiac major sound S2;
- extracting the characteristic, distinctly and in parallel, for both of said EA1 and EA2 components for each of said plurality of cycles;
- calculating the maximum average correlation coefficient for both said EA1 and EA2 components correlating said extracted characteristics of the first cycle of said plurality of cycles and said extracted characteristics of the second cycle of said plurality of cycles, for each of said EA1 and EA2 components respectively;
- performing relative temporal retiming of each EA sub-signal relative to said respective maximum average correlation coefficient; and
- delivering a readjusted EA1 component and a readjusted EA2 component associated with the plurality of EA sub-signals.

21. The non-transitory machine-readable storage medium of claim 20, wherein the operations further comprise determining an average global EA signal for a cycle, in response to said readjusted EA1 and EA2 components, and an average EA1 component and an average EA2 component, and combining said average EA1 and EA2 components so as to produce the average global EA signal for a cycle.

22. The non-transitory machine-readable storage medium of claim 21, wherein the operations further comprise determining temporal markers of characteristic moments in the cardiac cycle, starting from the aforementioned average global EA signal for a cycle.

23. The non-transitory machine-readable storage medium of claim 22, wherein said temporal markers comprise temporal markers correlated to moments of opening and closing of aortic, mitral, pulmonary and/or tricuspid valves.

* * * * *